(12) United States Patent
Riboulet et al.

(10) Patent No.: US 9,588,089 B2
(45) Date of Patent: Mar. 7, 2017

(54) METHOD FOR ANALYZING A CORK STOPPER FOR THE PRESENCE OF 2,4,6-TRICHLOROANISOLE AND DEVICE FOR PERFORMING THE SAME

(71) Applicant: CEVAQOE INVEST, Tournefeuille (FR)

(72) Inventors: Jean-Michel Riboulet, Tournefeuille (FR); Luiz Armando Dos Reis Alves, Brandao (PT)

(73) Assignee: CEVAQUE INVEST, Tournefeuille (FR)

( * ) Notice: Subject to any disclaimer, the term of this patent is extended or adjusted under 35 U.S.C. 154(b) by 193 days.

(21) Appl. No.: 14/456,017

(22) Filed: Aug. 11, 2014

(65) Prior Publication Data

US 2015/0047414 A1 Feb. 19, 2015

(30) Foreign Application Priority Data

Aug. 13, 2013 (FR) ...................... 13 57968

(51) Int. Cl.
| | |
|---|---|
| *G01N 30/72* | (2006.01) |
| *C08L 97/00* | (2006.01) |
| *G01N 30/16* | (2006.01) |
| *G01N 33/00* | (2006.01) |
| *G01N 30/12* | (2006.01) |

(Continued)

(52) U.S. Cl.
CPC ........ G01N 30/7206 (2013.01); C08L 97/007 (2013.01); G01N 30/16 (2013.01); G01N 33/0011 (2013.01); G01N 33/0036 (2013.01); B27K 5/001 (2013.01); B27K 7/00 (2013.01); G01N 30/12 (2013.01);

(Continued)

(58) Field of Classification Search
CPC ..... G01N 2001/2241; G01N 2030/062; G01N 2030/126; G01N 30/12; G01N 30/7206; G01N 33/0011; G01N 33/0036
See application file for complete search history.

(56) References Cited

U.S. PATENT DOCUMENTS 5,174,956 A * 12/1992 Konishi ............. B01D 11/0219
264/124
7,010,956 B2 * 3/2006 Head .................. G01N 33/0034
73/23.34

(Continued)

OTHER PUBLICATIONS

C. Lorenzo et al. "Non-destructive method to determine halophenols and haloanisoles in cork stopper by headspace sorptive extraction." Journal of Chromotography A, 1114 (2006) 250-254.*

(Continued)

*Primary Examiner* — Natalie Huls
(74) *Attorney, Agent, or Firm* — Im IP Law; C. Andrew Im

(57) ABSTRACT

A non-destructive method for analyzing a cork stopper for the presence of 2,4,6-trichloroanisole. The stopper is introduced into a hermetically closed container. The container containing the stopper is heated under conditions vaporizing any 2,4,6-trichloroanisole present in the stopper. A gaseous sample of the atmosphere surrounding the stopper in the container is collected and analyzed for the presence of 2,4,6-trichloroanisole. This method allows the selection, in a batch of cork stoppers, of the stoppers that are substantially free of 2,4,6-trichloroanisole, in a non-destructive manner.

11 Claims, 2 Drawing Sheets

(51) Int. Cl.
  *G01N 30/06* (2006.01)
  *G01N 1/22* (2006.01)
  *B27K 5/00* (2006.01)
  *B27K 7/00* (2006.01)

(52) U.S. Cl.
  CPC ............... *G01N 2001/2241* (2013.01); *G01N 2030/062* (2013.01); *G01N 2030/126* (2013.01)

(56) References Cited

U.S. PATENT DOCUMENTS

| | | | | |
|---|---|---|---|---|
| 7,971,470 | B2* | 7/2011 | Broz | G01N 33/46 73/23.22 |
| 2004/0090231 | A1* | 5/2004 | Augustine | G01N 24/08 324/309 |
| 2005/0092112 | A1 | 5/2005 | Head et al. | |
| 2008/0245132 | A1* | 10/2008 | Head | G01N 33/46 73/23.34 |
| 2009/0038374 | A1 | 2/2009 | Broz | |
| 2012/0037804 | A1* | 2/2012 | Federici | G01N 21/3586 250/341.1 |
| 2014/0224759 | A1* | 8/2014 | Aagaard | B65D 39/0011 215/43 |
| 2015/0000371 | A1* | 1/2015 | Greene | G01N 33/146 73/19.1 |
| 2015/0293067 | A1* | 10/2015 | Greene | G01N 21/61 356/72 |
| 2016/0018375 | A1* | 1/2016 | Fahrni | G01N 1/2226 73/37 |

OTHER PUBLICATIONS

Lorenzo et al., "Non-destructive method to determine halophenols and haloanisoles in cork stoppers by headspace sorptive extraction", Journal of Chromatography, May 12, 2006, pp. 250-254, vol. 1114, No. 2, Elsevier Science Publishers, Netherlands.

Pizarro et al., "Optimisation of a microwave-assisted extraction method for the simultaneous determination of haloanisoles and halophenols in cork stoppers", Journal of Chromatography, Apr. 26, 2007, pp. 138-144, vol. 1149, No. 2, Elsevier Science Publishers, Netherlands.

Riu et al., "Quantification of chloroanisoles in cork using headspace solid-phase microextraction and gas chromatography with electron capture detection", Journal of Chromatography, Feb. 24, 2006, pp. 240-247, vol. 1107, No. 1-2, Elsevier Science PUblishers, Netherlands.

* cited by examiner

METHOD FOR ANALYZING A CORK STOPPER FOR THE PRESENCE OF 2,4,6-TRICHLOROANISOLE AND DEVICE FOR PERFORMING THE SAME

RELATED APPLICATIONS

This application claims priority from French Patent Application No. 13 57968 filed Aug. 13, 2013, which is herein incorporated by reference in its entirety.

FIELD OF THE INVENTION

The present invention lies in the field of controlling the quality of cork stoppers, which are intended especially for stoppering wine bottles. More particularly, the invention relates to a method for analyzing a cork stopper for the presence of 2,4,6-trichloroanisole, and also to a device for performing such a method. The invention also relates to a more global process for selecting, in a batch of cork stoppers, stoppers that are substantially free of 2,4,6-trichloroanisole, this process involving the steps of a method for analyzing a cork stopper according to the invention.

BACKGROUND OF THE INVENTION

Cork stoppers have been extensively used for stoppering containers containing food products, more particularly bottles containing drinks, and in particular wine, for many years. Cork, a natural material which constitutes the bark of the cork oak tree *Quercus suber*, has properties that are particularly advantageous for this purpose, especially properties of impermeability to liquids, lightness and mechanical properties of elasticity, resilience and compressibility.

In the present description, the term "cork stopper" means both stoppers consisting exclusively of cork and stoppers made of a material based on cork, of which cork is a major component.

The use of cork stoppers for stoppering bottles of liquid may occasionally give rise to a negative effect regarding the quality of the liquid stored, in particular when this liquid is wine, more specifically impairments of its odor and/or taste. In the field of oenology, these impairments are commonly referred to by the term "corky flavor". It has been demonstrated that the corky flavor is mainly due to the presence in the cork constituting the stopper of a contaminating aromatic molecule, 2,4,6-trichloroanisole (TCA), which is released by the stopper and which interacts with the wine to modify its organoleptic properties. This molecule originates from the methylation of chlorophenols, which may be derived from various origins.

A very small content of TCA in the wine suffices for consumers to detect a corky flavor therein: the detection threshold for TCA by the human nose is in fact very low, less than 4 ng/l. It is therefore a major challenge for the wine industry to minimize as much as possible the contamination by TCA of cork stoppers used for stoppering bottles, especially wine bottles.

The prior art has proposed various methods for treating cork, prior to forming it into a stopper, which are directed toward ridding it of its aromatic organic contaminants, especially TCA. However, despite the efforts deployed, it has not been possible hitherto to ensure total decontamination of cork stoppers, in particular with respect to TCA.

It is thus recommended, before using cork stoppers for stoppering bottles for conserving a food liquid, and more particularly wine, to test these stoppers for the presence of 2,4,6-trichloroanisole, and thus to anticipate beforehand the risk of impairment of the quality of the liquid associated with the stoppers. Such an analysis is nowadays considered as essential in controlling the quality of cork stoppers.

The main technique proposed by the prior art for this purpose, and which is the subject of standard ISO 20752 ("cork stoppers—assay of releasable 2,4,6-trichloroanisole (TCA)"), consists in taking, in a batch of stoppers, a sample of stoppers, typically composed of twenty stoppers, and in macerating it in a solution simulating wine, more specifically an aqueous-alcoholic solution, so as to simulate the phenomena of migration of TCA that are liable to take place between the cork stoppers and the wine. An aliquot of the macerate thus obtained is sampled via the solid-phase microextraction technique and then analyzed by gas chromatography, with detection by mass spectrometry or electron uptake. Such a method, commonly referred to by the abbreviation SPME, is, however, long to implement. In addition, on account of its destructive nature on stoppers, it can only be performed on a limited number of stoppers from a given batch of stoppers. It therefore gives only a globalized result about the contamination of the batch, and does not at all guarantee that each individual stopper of the batch of stoppers is free from contamination with 2,4,6-trichloroanisole.

A process was moreover proposed in the publication by Lorenzo et al. (2006) Journal of Chromatography, 114: 250-254, for the analysis of a cork stopper for the presence of haloanisoles, especially 2,4,6-trichloroanisole, via successive steps of: heating the stopper in a flask in which is also placed, above the stopper, a bar coated with a layer of polydimethylsiloxane (PDMS); absorption onto this bar of the vapors of certain volatile chemical compounds escaping from the stopper during heating; thermal desorption of these chemical compounds; analysis of these compounds by gas chromatography coupled to mass spectrometry. Such a process however proves to be complex, long and expensive to implement. Moreover, it does not make it possible to obtain reliable results regarding the amount of haloanisoles initially contained in the stopper, on account of the losses of compounds occurring during the steps of adsorption/desorption on the bar.

The present invention is directed toward overcoming the drawbacks of the methods for analyzing cork stoppers for the presence of 2,4,6-trichloroanisole proposed in the prior art, especially those presented hereinabove, by proposing such a method which allows reliable and sensitive detection of the presence of 2,4,6-trichloroanisole in cork stoppers, and, where appropriate, the assay thereof, while at the same time being non-destructive, i.e. it does not impair the chemical, physical or organoleptic properties of the cork, and as such is able to be performed on each individual stopper of a batch of stoppers, ensuring that this stopper remains usable for the subsequent stoppering of bottles, especially wine bottles. The invention is also directed toward ensuring that this process can be totally, or at least partially, automated, easily, quickly and at reduced cost.

SUMMARY OF THE INVENTION

Thus, according to a first aspect, the present invention relates to a method for analyzing a cork stopper for the presence of 2,4,6-trichloroanisole, which comprises the succession of the following steps:
  introduction of the stopper into a container,
  hermetic closure of the container, heating of the container containing the stopper under conditions, in particular in terms of temperature, pressure and time, which allow vaporization of 2,4,6-trichloroanisole that might be present in the stopper, more precisely of at least part of any 2,4,6-trichloroanisole present in the stopper, collection of a gaseous sample of the atmosphere surrounding the stopper in the container, and analysis of the gaseous sample thus collected for the presence of 2,4,6-trichloroanisole.

The method according to the invention especially advantageously envisages the collection of a gaseous sample of the atmosphere surrounding the stopper in the container, i.e. of a fraction of the overall atmosphere present in the container and surrounding the stopper. The sample thus has a composition identical to the overall composition of the atmosphere present in the container. The invention thereby differs especially from the processes proposed in the prior art, which perform the selective sampling, in the container in which the stopper is placed, of particular compounds present in the atmosphere. Contrary to what such processes permit, the gaseous sample thus collected according to the invention especially offers the advantage of being able to be used directly for the subsequent analysis step, without needing to undergo beforehand an additional treatment step, and as such the method according to the invention is simpler, faster, more reliable and less expensive to implement.

In particular, the method according to the invention advantageously does not comprise a step of introducing into the container any element other than the stopper, especially a PDMS bar.

It does not comprise, either, a step of introducing a liquid component into the container containing the stopper, in particular such as an aqueous-alcoholic solution. Thus, the heating of the stopper hermetically enclosed in the container is performed under dry conditions. This method is advantageously not destructive: its implementation does not bring about any degradation of the properties of the cork, and as such the stopper that has been subjected to this process can then be used normally for stoppering bottles, without prior treatment.

It falls within the competence of a person skilled in the art to determine the combinations of temperature, pressure and time conditions that allow vaporization of 2,4,6-trichloroanisole that might be present in the stopper, as a function especially of the vaporization temperature of the same, which is known per se, and of the desired speed for the analysis of the stopper.

According to particular embodiments, the method according to the invention also satisfies the following characteristics, implemented separately or in each of the technically operative combinations thereof.

The temperature, pressure and time conditions to which the container containing the stopper is subjected during the heating step are advantageously chosen so as to ensure the establishment of an equilibrium between the 2,4,6-trichloroanisole contained in the stopper and the 2,4,6-trichloroanisole in gaseous form present in the atmosphere surrounding the stopper in the container. The step of collecting the gaseous sample in the atmosphere surrounding the stopper in the container is then performed after this equilibrium has been established.

In particular embodiments of the invention, the heating of the container containing the stopper is performed at a temperature of between 50 and 75° C., at atmospheric pressure and for a time of between 45 and 90 minutes and preferably of about 60 minutes. Such operating conditions advantageously make it possible to vaporize 2,4,6-trichloroanisole that might be contained in the stopper, including when it is present therein in small contents, while at the same time preserving the integrity and properties of the stopper, and ensuring the establishment of an equilibrium between the 2,4,6-trichloroanisole contained in the stopper and the 2,4,6-trichloroanisole in gaseous form present in the atmosphere surrounding the stopper in the container.

The step of analyzing the gaseous sample for the presence of 2,4,6-trichloroanisole of the method according to the invention may comprise the quantification of the 2,4,6-trichloroanisole present in this gaseous sample. This quantification may be absolute, by comparison of the sample with a calibration range of compositions of known 2,4,6-trichloroanisole concentrations, or relative.

The step of analyzing the gaseous sample for the presence of 2,4,6-trichloroanisole may be performed via any technique that is standard per se. In particular embodiments of the invention, it is performed by gas chromatography coupled to a detection method. The gaseous sample collected in the container is injected directly into the gas chromatograph, i.e. without being subjected to any treatment step, especially a step of desorption from any element.

The method of detection coupled to gas chromatography is conventional per se. It may be chosen especially from mass spectrometry, electron uptake, ion mobility spectrometry and ion mobility mass spectrometry, such methods having the advantages of being quick to implement, reliable and having a high detection sensitivity.

The separation of the components contained in the gaseous sample by gas chromatography may especially be performed using a column of polydimethylsiloxane. The chromatography conditions may be readily determined by a person skilled in the art, as a function especially of the speed with which he wishes the analysis to be performed.

In an entirely advantageous manner, in the case where the analysis step uses a gas chromatograph, the collection of a gaseous sample in the container containing the stopper to be analyzed is preferentially performed directly with the syringe of the chromatograph injection system, for direct injection into the head of the column. To this end, the preliminary step of hermetic closure of the container in which the stopper was placed uses closure means equipped with a wall that can be pierced with the syringe needle, for example a septum.

Preferentially, the method according to the invention is performed in a partially or totally automated manner. In particular, the steps of heating, of collection of the gaseous sample and of analysis are performed automatically, and the supplying of a sample to the heating means, the collection means and the analysis means is also performed automatically.

The method according to the invention advantageously has a detection sensitivity at least as good as that of the methods proposed in the prior art, especially the SPME method. The method according to the invention especially makes it possible to achieve a 2,4,6-trichloroanisole detection threshold equivalent to a value of 0.5 ng/l obtained by the SPME method, and a 2,4,6-trichloroanisole quantification threshold equivalent to a value of 1.0 ng/l obtained by the SPME method.

According to another aspect, the present invention relates to a more global selection process for selecting, in a batch of cork stoppers, stoppers that are substantially free of 2,4,6-trichloroanisole, which comprises the succession of the following steps:

implementation, for each of the stoppers of the batch, of method for analyzing a cork stopper according to the invention, which satisfies one or more of the characteristics above, and selection, in the batch of stoppers, of the stoppers for which the presence of 2,4,6-trichloroanisole is not detected.

In particular embodiments of the invention, the selection process also comprises the determination, for each of the stoppers of the batch, of a value representative of the concentration of 2,4,6-trichloroanisole in the gaseous sample. This representative value may consist, for example, of the area under a detected peak, at the retention time corresponding to 2,4,6-trichloroanisole, by gas chromatography with detection by electron uptake. For the stoppers for which this representative value is not zero, the selection process may then comprise:

the comparison of this representative value with a predetermined threshold value, and the selection of the stoppers for which the representative value is less than or equal to the threshold value.

Such a process for implementing the individual control of the contamination of all of the stoppers of the batch of stoppers makes it possible to select, for a subsequent use, only the stoppers that are guaranteed to be substantially free of 2,4,6-trichloroanisole. The term "substantially free of" means that the stoppers are free of 2,4,6-trichloroanisole, or contain a low content of this contaminant, less than a threshold value that is predetermined according to the particular application intended for the batch of stoppers.

The process according to the invention thus makes it possible to develop a reliable and real conclusion in terms of distribution of the stoppers according to the frequency and concentration of any contamination with 2,4,6-trichloroanisole, in contrast with the SPME method proposed by the prior art and which is the subject of standard ISO 20752, which makes it possible to develop only an approximate conclusion with statistical reasoning.

The selection process may also comprise a step of sorting the containers, according to the results of the analysis of the gaseous samples that are collected therefrom for the presence of 2,4,6-trichloroanisole, this step preferably being performed automatically. In particular, this step may consist in dividing the containers into several groups, including at least one group for which the presence of 2,4,6-trichloroanisole is not detected, and one group for which the presence of 2,4,6-trichloroanisole is detected. The process may also envisage dividing the latter group into several subgroups, corresponding firstly to the stoppers for which the representative value is less than or equal to a predetermined threshold value, and secondly to the stoppers for which the representative value is greater than said predetermined threshold value.

The selection process may also comprise a step of opening the containers and recovering the stoppers contained therein, which is also preferably performed automatically.

According to another aspect, the present invention relates to a device for performing a method for analyzing a cork stopper for the presence of 2,4,6-trichloroanisole, and/or a selection process, according to the invention. This device comprises:

an automated heating module for heating a container in which a stopper is placed, under conditions allowing vaporization of 2,4,6-trichloroanisole that might be present in said stopper, an automated sample collection module for collecting a gaseous sample of the atmosphere surrounding the stopper in the container, an automated module for analyzing the gaseous sample thus collected for the presence of 2,4,6-trichloroanisole, where appropriate, automated means for conveying the container containing the stopper to the heating module and/or from the heating module to the sample collection module, and where appropriate, an automated module for sorting the containers according to the results of the analysis for the presence of 2,4,6-trichloroanisole.

In particular embodiments of the invention, the device also comprises an automated module for introducing a stopper into a container and/or a module for hermetically closing the container into which the stopper has been introduced.

All of the device modules and conveying means according to the invention are standard per se.

The module for analyzing the gaseous sample collected in the container for the presence of 2,4,6-trichloroanisole may especially comprise a gas chromatograph coupled to detection means. These detection means are standard per se, and may be chosen especially from mass spectrometers, electron uptake detectors, ion mobility spectrometers and ion mobility mass spectrometers. The automated module for collecting a gaseous sample in the container then comprises an automatic injection system of the gas chromatograph.

Preferentially, the automated module for collecting the gaseous sample in the container is the automatic injection system of the gas chromatograph. This injection system then advantageously performs the collection of the gaseous sample of the atmosphere present in the container around the stopper to be analyzed, and the injection of this sample directly into the chromatograph.

In preferred embodiments of the invention, the device comprises at least two automated modules for analyzing gaseous samples collected from the containers, which are mounted in parallel, and used alternately, so as to be able to analyze at least twice as many gaseous samples in the same time interval.

The device may also comprise a module for opening the containers and for extracting the stoppers contained therein.

In embodiments of the invention that are particularly advantageous for the industrial implementation of the method according to the invention, the device also comprises a module for the automatic control of the automated modules included in the device according to the invention and, where appropriate, of the conveying means.

In particular, this automatic control module comprises means for slaving the module for sorting the containers to the analytical results of the gaseous samples for the presence of 2,4,6-trichloroanisole.

The various steps of data memorization, of comparison of the measured values with the predetermined threshold values, and of control of the various modules are preferably performed by a module of the programmed computer type, comprising at least a microprocessor, and memorization means (magnetic hard drive, flash memory, optical disk, etc.) in which is memorized a computer program product, in the form of a set of program code instructions to be run so as to perform the various calculation and control steps of the method according to the invention.

A device satisfying such characteristics advantageously makes it possible to perform the method for analyzing a cork stopper according to the invention continuously and in series on a large number of stoppers to be individually analyzed.

BRIEF DESCRIPTION OF THE DRAWINGS

The characteristics and advantages of the invention will emerge more clearly in light of the implementation example below, which is given purely as an illustration of the invention and in no way limiting the same, with the support of FIGS. 1 to 3, in which:

FIG. 2b shows a chromatogram obtained for a 2 ng/l solution of 2,4,6-trichloroanisole in ethanol, analyzed under the same conditions as for the production of the chromatogram of FIG. 2a.

DETAILED DESCRIPTION OF THE INVENTION

A method according to the invention for analyzing a cork stopper for the presence of 2,4,6-trichloroanisole comprises the following steps.

Firstly, a cork stopper is placed in a container 11, for example having a volume of 100 ml.

This container 11 is hermetically closed, especially using a closing member suited to the injection system of a gas chromatograph.

These first steps may be performed manually or in an automated manner, by adequate automatic modules that are standard per se for the introduction in series of solid articles into individual containers and the closure of these containers.

The container 11 containing a stopper is then subjected to a step of heating, at a temperature of between 50 and 75° C., more precisely at 70° C., at atmospheric pressure, for 1 h. These heating conditions bring about the release of at least part of the 2,4,6-trichloroanisole that may be contained in the cork, in gaseous form, in the internal atmosphere of the container 11, and the stabilization in an equilibrium state.

A sample, for example 0.5 ml, of the atmosphere present in the container 11 containing the stopper, is then collected from the container 11 and analyzed for the presence of 2,4,6-trichloroanisole.

This analysis is performed, for example, by gas chromatography and detection by electron uptake.

Figure 1:
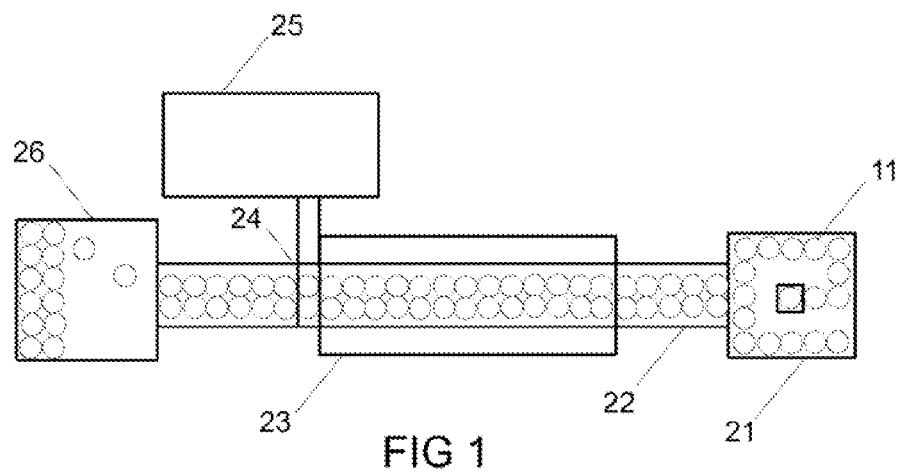
FIG. 1 schematically shows an automated device for performing the final steps of a method according to the invention for analyzing a cork stopper for the presence of 2,4,6-trichloroanisole.

An example of a device for the serial and automated implementation of these steps of the method according to the invention is shown schematically in FIG. 1.

This device comprises a module 21 for receiving containers 11 each containing a cork stopper.

From this reception module 21, the containers 11 are transported, via a conveyor 22, which is standard per se, through a heating tunnel 23. This heating tunnel may be of any type that is standard per se.

The heating power of the heating tunnel 23 and the speed of the conveyor 22 are adjusted so that each container 11 is subjected, in the heating tunnel 23, to a temperature of between 50 and 75° C. for 1 h.

At the exit of the heating tunnel 23, the container 11 is conveyed, still by the conveyor 22, to a sample collection module 24 for the collection of a gaseous sample of the internal atmosphere of the container 11 surrounding the stopper. This collection is preferentially performed by the automatic injection system of a gas chromatograph. In FIG. 1, reference 25 denotes, as a whole, this chromatograph and a combined detector.

The gaseous sample thus collected is injected into the chromatograph, and analyzed for the presence of 2,4,6-trichloroanisole.

On exiting the sample collection module 24, the container 11, still containing the stopper, is transported by the conveyor 22 to a module 26 for collecting the containers, in order to sort them as a function of the results of the analysis by gas chromatography.

The device may also comprise a sorting module for the automated sorting of the containers, as a function of the results of the analysis for the presence of 2,4,6-trichloroanisole performed by the gas chromatograph and the associated detector. This sorting module, which is not shown in the figures, is advantageously controlled by a control module which the device comprises. The control module is especially capable of acquiring the data recorded by the detector for each container 11, processing them and emitting, for each container 11, a control signal to the sorting module, established as a function of the result of the analysis for the presence of 2,4,6-trichloroanisole, so as to ensure separation of the containers 11 as a function of the presence of 2,4,6-trichloroanisole in the stoppers they contain, and/or of the measured concentration of TCA.

The gas chromatograph 25 is conventional per se.

It is equipped, for example, with two analytical pathways, each being composed of an injector, an injection valve, a short capillary column and a detector, for example by electron uptake. This advantageously makes it possible to perform two analyses simultaneously. Preferentially, the two analytical pathways are managed by the same control module.

By way of example, an ordinary cork stopper was subjected to the above steps. The gaseous sample collected from the container 11 containing it was analyzed by gas chromatography, on a polydimethylsiloxane column with a phase thickness of 5 μm, coupled to an electron-uptake detector. A 2 ng/L calibration solution of 2,4,6-trichloroanisole in ethanol was also prepared and injected into the chromatograph, under the same operating conditions.

Figure 2A:
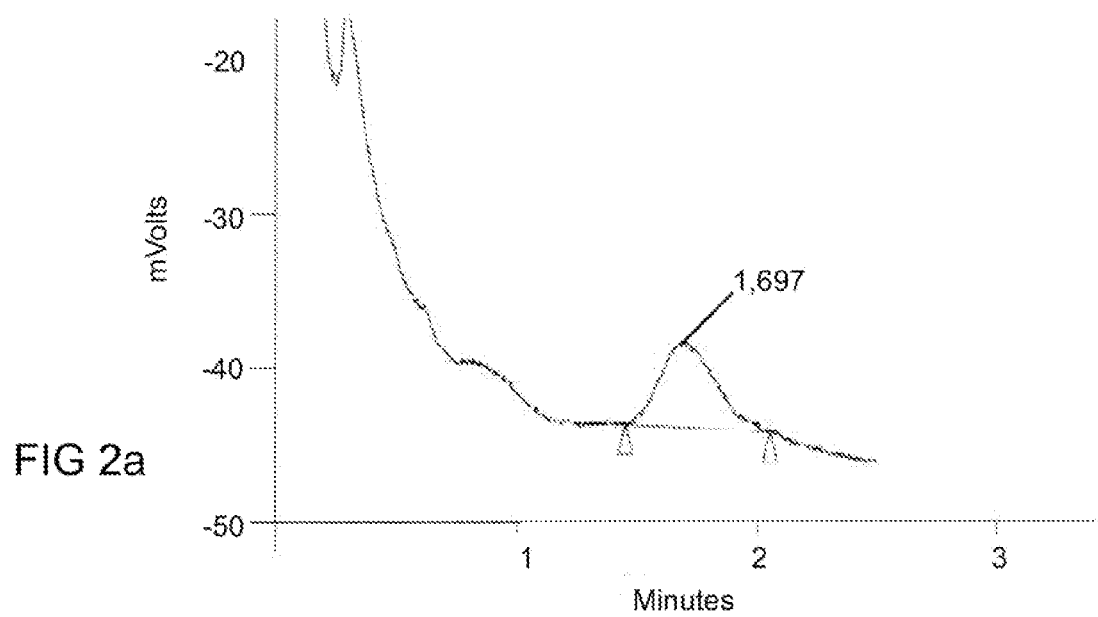
FIG. 2a shows an example of a chromatogram obtained after performing a method according to the invention, for analyzing a cork stopper for the presence of 2,4,6-trichloroanisole.
Figure 2B:
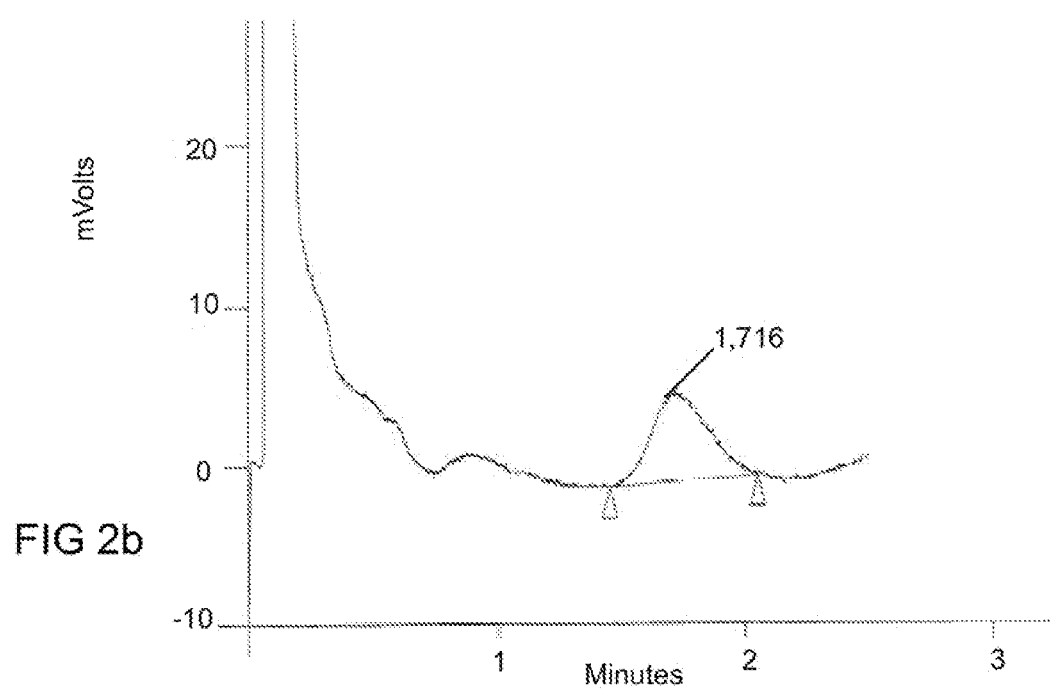

The chromatograms obtained are shown in FIG. 2a for the sample treated in accordance with the invention, and in FIG. 2b for the 2,4,6-trichloroanisole calibration solution.

It is seen in these figures that the chromatogram obtained according to the invention has a peak at 1.697 minutes, which may indeed be attributed to 2,4,6-trichloroanisole, the control chromatogram of which shows a retention time of 1.716 minutes.

In a more global selection process, in a batch of cork stoppers, stoppers substantially free of 2,4,6-trichloroanisole, this stopper is discarded since it is contaminated with 2,4,6-trichloroanisole and thus liable to give wine a corky flavor.

The quantification of the content of 2,4,6-trichloroanisole in the stopper may be performed, for example, by measuring the area under the peak obtained at the retention time corresponding to 2,4,6-trichloroanisole, and comparison with a calibration range of compositions with known concentrations of 2,4,6-trichloroanisole.

A comparative analysis by gas chromatography coupled to mass spectrometry is also performed on a gaseous sample collected in the container in accordance with the present invention, and on a control of pure 2,4,6-trichloroanisole. The mass spectrometer functions in MS/MS mode, with a chamber temperature of 45° C. and an ion trap analyzer temperature of 150° C. Identical mass spectra are obtained for the sample obtained in accordance with the invention and for the 2,4,6-trichloroanisole control, which confirms that the method according to the invention makes it possible to detect and quantify the 2,4,6-trichloroanisole present in the cork stopper. More specifically, a peak is found at 197 m/z in both spectra, corresponding to the fragmentation of the parent ion at 212 m/z of 2,4,6-trichloroanisole.

The quantification of the 2,4,6-trichloroanisole content of the stopper may be performed, for example, by measuring the intensity of this peak at 197 m/z, and comparison with a calibration range of compositions with known concentrations of 2,4,6-trichloroanisole.

A comparative analysis was also performed with the SPME method proposed in the prior art. To this end, ten cork stoppers were subjected to the method according to the invention, as described above. For each, the gaseous sample was analyzed by gas chromatography coupled to electron-uptake detection. The area of the peak corresponding to 2,4,6-trichloroanisole was measured.

The stoppers were then recovered and were each subjected to the SPME method, according to the standard protocol described in standard ISO 20752. The 2,4,6-trichloroanisole concentration, expressed in ng/l, was measured.

The results obtained for each of the stoppers, by each of the techniques, are indicated in table 1 below.

TABLE 1

Result of the analysis of the 2,4,6-trichloroanisole content of cork stoppers, by the SPME method of the prior art and by the method according to the invention

| Stopper | SPME method (ng/l) | Method according to the invention (area of the peak) |
| --- | --- | --- |
| 1 | 0.3 | 0 |
| 2 | 0.4 | 0 |
| 3 | 1.0 | 9 425 |
| 4 | 3.5 | 84 429 |
| 5 | 3.6 | 83 334 |
| 6 | 4.8 | 101 827 |
| 7 | 6.6 | 145 207 |
| 8 | 7.7 | 191 720 |
| 9 | 11.7 | 306 605 |
| 10 | 20.4 | 545 914 |

From the values thus obtained, a curve representing the area under the peak was plotted for each stopper.

Figure 3:
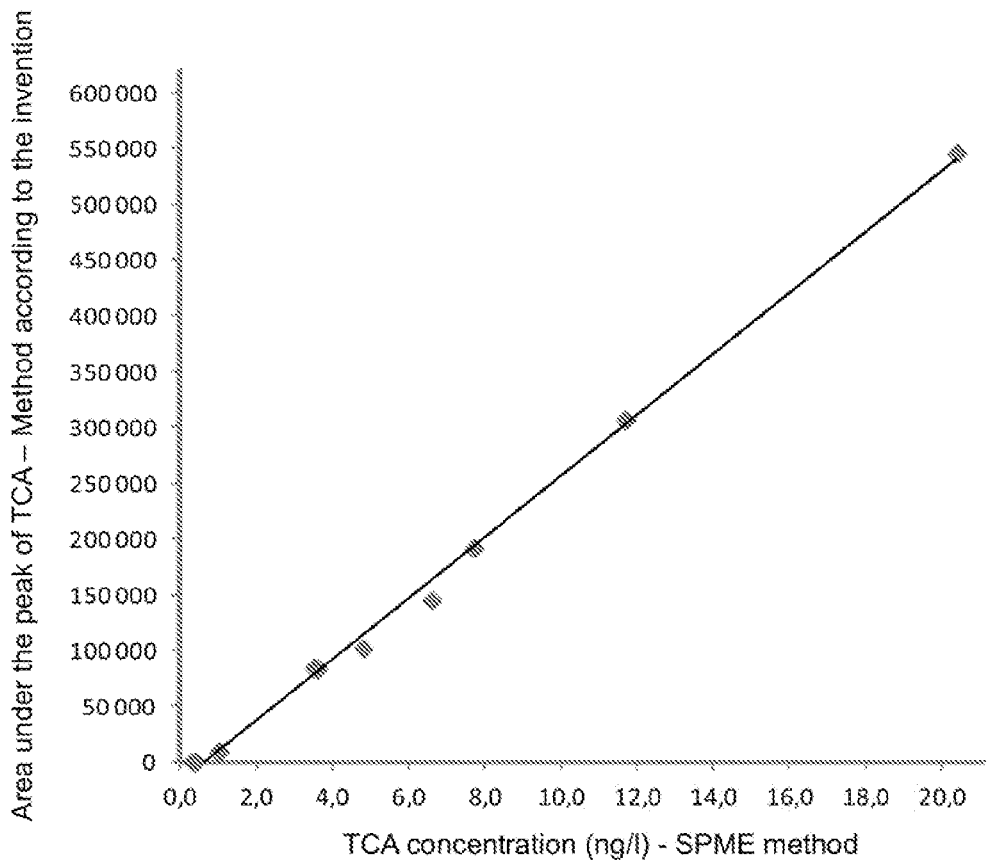
FIG. 3 shows a graph representing, for 10 stoppers individually analyzed, successively by a method in accordance with the invention and by the SPME method of the prior art, the area under the peak measured at the retention time of 2,4,6-trichloroanisole by performing the method according to the invention, as a function of the concentration of 2,4,6-trichloroanisole measured by the SPME method.

The values obtained for each stopper were reported on a graph, the concentration obtained via the SPME method being given on the x-axis and the area under the peak obtained in accordance with the invention being represented on the y-axis. The graph obtained is shown in FIG. 3. Perfect agreement between the values obtained via the method according to the invention and those obtained via the SPME method of the prior art is clearly seen therein.

The method for analyzing a cork stopper according to the invention thus makes it possible to quantify the 2,4,6-trichloroanisole present in a cork stopper as reliably as the SPME method.

It also has many advantages over the prior art methods, and especially the SPME method. It especially makes it possible to analyze up to 1440 stoppers in 24 hours for the presence of 2,4,6-trichloroanisole. It comprises few steps, which can all be performed easily, quickly and, what is more, automatically. It does not use any consumables, or reagents, such as a maceration solution or solid-phase microextraction fibers.

Finally, and above all, it allows the analysis of each stopper of a batch individually, without impairing the properties of this stopper. It thus ensures that each stopper that it selects is free, or substantially free, of 2,4,6-trichloroanisole and will have no incidence on the taste and/or odor of wine conserved in the bottle that this stopper will serve to stopper.

The invention claimed is:

1. A method for analyzing a cork stopper for a presence of 2,4,6-trichloroanisole, comprising the steps of successively:
   introducing only the cork stopper into a container;
   hermetically closing the container;
   heating the container containing the cork stopper to vaporize any 2,4,6-trichloroanisole present in the cork stopper;
   collecting a gaseous sample of an atmosphere surrounding the cork stopper in the container, by collecting a fraction of an overall atmosphere present in the container and surrounding the cork stopper, said gaseous sample having a composition identical to the composition of the atmosphere; and
   analyzing the gaseous sample for the presence of 2,4,6-trichloroanisole.

2. The method as claimed in claim 1, further comprising the step of heating the container containing the cork stopper at a temperature of between 50 and 75° C., at atmospheric pressure and for a time between 45 and 90 minutes.

3. The method as claimed in claim 2, further comprising the step of heating the container containing the cork stopper at the temperature of between 50 and 75° C., at the atmospheric pressure and for 60 minutes.

4. The method as claimed in claim 1, wherein the step of analyzing the gaseous sample comprises the step of quantifying the 2,4,6-trichloroanisole present in the gaseous sample.

5. The method as claimed in claim 1, wherein the step of analyzing the gaseous sample for the presence of 2,4,6-trichloroanisole comprises the step of performing a gas chromatography by injecting the gaseous sample collected in the container directly into a gas chromatograph coupled to a detector.

6. The method as claimed in claim 5, further comprising the step of selecting a detection method utilized by the detector from one of the following: a mass spectrometry, an electron uptake, an ion mobility spectrometry or an ion mobility mass spectrometry.

7. The method as claimed in claim 1, wherein the steps are performed in an automated manner.

8. The method as claimed in claim 1, wherein the step of hermetically closing the container is performed using a closure equipped with a wall that can be pierced with a syringe needle.

9. The method as claimed in claim 1, wherein the step of analyzing the gaseous sample for the presence of 2,4,6-trichloroanisole comprises the step of performing a gas chromatography; and wherein the step of collecting the gaseous sample of the atmosphere surrounding the cork stopper in the container is performed directly with a syringe of a gas chromatograph injection system.

10. A process for selecting cork stoppers from a batch of cork stoppers that are substantially free of 2,4,6-trichloroanisole, comprising the steps of successively:

analyzing each cork stopper in the batch for the presence of 2,4,6-trichloroanisole as claimed in claim 1; and selecting said each cork stopper when the presence of 2,4,6-trichloroanisole is not detected.

11. The selection process as claimed in claim 10, further comprising the steps of determining a value representative of a concentration of 2,4,6-trichloroanisole in the gaseous sample for said each cork stopper in the batch; and additionally performing the following steps for said each cork stopper having a non-zero representative value:

comparing the representative value of said each cork stopper with a predetermined threshold value; and selecting said each cork stopper having the representative value which is less than or equal to the threshold value.

* * * * *

(12) EX PARTE REEXAMINATION CERTIFICATE (11428th)
United States Patent
Riboulet et al.

(10) Number: US 9,588,089 C1
(45) Certificate Issued: Dec. 11, 2018

(54) METHOD FOR ANALYZING A CORK STOPPER FOR THE PRESENCE OF 2,4,6-TRICHLOROANISOLE AND DEVICE FOR PERFORMING THE SAME

(71) Applicant: CEVAQOE INVEST, Tournefeuille (FR)

(72) Inventors: Jean-Michel Riboulet, Tournefeuille (FR); Luiz Armando Dos Reis Alves, Brandao (PT)

(73) Assignee: CEVAQOE INVEST, Tournefeuille (FR)

Reexamination Request:
No. 90/014,111, Mar. 13, 2018

Reexamination Certificate for:
Patent No.: 9,588,089
Issued: Mar. 7, 2017
Appl. No.: 14/456,017
Filed: Aug. 11, 2014

(30) Foreign Application Priority Data

Aug. 13, 2013 (FR) ..................... 13 57968

(51) Int. Cl.
*G01N 30/72* (2006.01)
*G01N 33/00* (2006.01)
*C08L 97/00* (2006.01)
*G01N 30/16* (2006.01)
*G01N 30/12* (2006.01)
*G01N 30/06* (2006.01)
*G01N 1/22* (2006.01)
*B27K 5/00* (2006.01)
*B27K 7/00* (2006.01)

(52) U.S. Cl.
CPC ........ *G01N 30/7206* (2013.01); *C08L 97/007* (2013.01); *G01N 30/16* (2013.01); *G01N 30/72* (2013.01); *G01N 33/0011* (2013.01); *G01N 33/0036* (2013.01); *B27K 5/001* (2013.01); *B27K 7/00* (2013.01); *G01N 30/12* (2013.01); *G01N 2001/2241* (2013.01); *G01N 2030/062* (2013.01); *G01N 2030/126* (2013.01)

(58) Field of Classification Search
None
See application file for complete search history.

(56) References Cited

To view the complete listing of prior art documents cited during the proceeding for Reexamination Control Number 90/014,111, please refer to the USPTO's public Patent Application Information Retrieval (PAIR) system under the Display References tab.

*Primary Examiner* — Cameron Saadat

(57) ABSTRACT

A non-destructive method for analyzing a cork stopper for the presence of 2,4,6-trichloroanisole. The stopper is introduced into a hermetically closed container. The container containing the stopper is heated under conditions vaporizing any 2,4,6-trichloroanisole present in the stopper. A gaseous sample of the atmosphere surrounding the stopper in the container is collected and analyzed for the presence of 2,4,6-trichloroanisole. This method allows the selection, in a batch of cork stoppers, of the stoppers that are substantially free of 2,4,6-trichloroanisole, in a non-destructive manner.

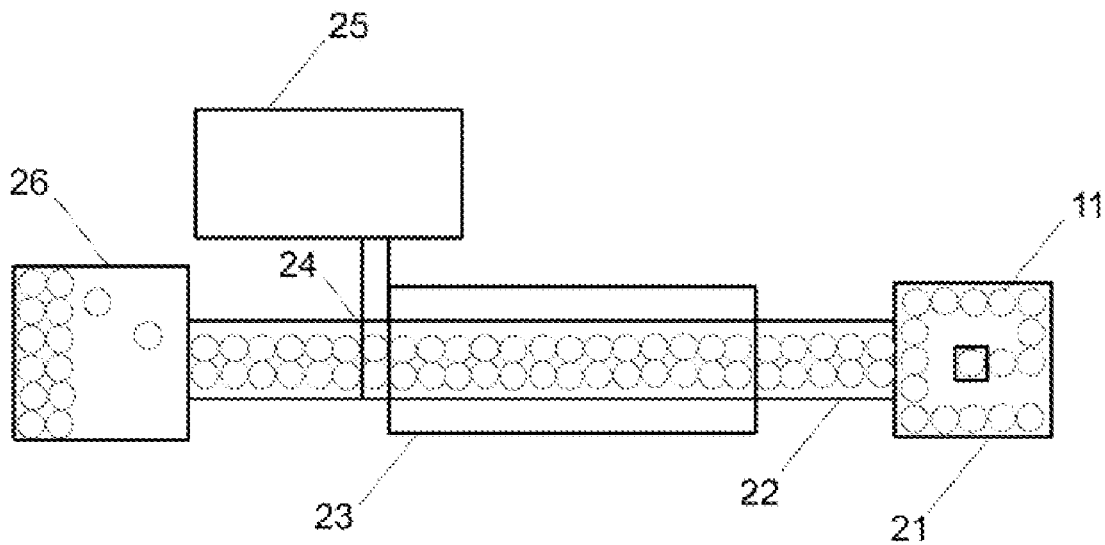

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10 and 11 are determined to be patentable as amended.

Claims 2-9, dependent on an amended claim, are determined to be patentable.

New claim 12 is added and determined to be patentable.

1. A *non-destructive* method for analyzing a cork stopper for a presence of 2,4,6-trichloroanisole, comprising the steps of successively:
   introducing only the cork stopper into a container;
   hermetically closing the container;
   heating the container containing the cork stopper to vaporize any 2,4,6-trichloroanisole present in the cork stopper;
   collecting a gaseous sample of an atmosphere surrounding the cork stopper in the container, by collecting a fraction of an overall atmosphere present in the container and surrounding the cork stopper, said gaseous sample having a composition identical to the composition of the atmosphere; and
   analyzing the gaseous sample for the presence of 2,4,6-trichloroanisole, *the cork stopper remaining usable for a subsequent stoppering of bottles.*

10. A process for selecting cork stoppers from a batch of cork stoppers that are substantially free of 2,4,6-trichloroanisole, comprising the steps of successively:
    analyzing each cork stopper in the batch for the presence of 2,4,6-trichloroanisole as claimed in claim 1; [and]
    selecting said each cork stopper when the presence of 2,4,6-trichloroanisole is not detected*; and*
    *recovering said selected each cork stopper.*

11. The selection process as claimed in claim 10, further comprising the steps of determining a value representative of a concentration of 2,4,6-trichloroanisole in the gaseous sample for said each cork stopper in the batch; and additionally performing the following steps for said each cork stopper having a non-zero representative value:
    comparing the representative value of said each cork stopper with a predetermined threshold value; [and]
    selecting said each cork stopper having the representative value which is less than or equal to the threshold value*; and*
    *recovering said selected each cork stopper.*

12. *The method as claimed in claim 1, implemented before using the cork stopper for stoppering a bottle.*

* * * * *